United States Patent [19]

Parratt

[11] Patent Number: 4,548,909
[45] Date of Patent: Oct. 22, 1985

[54] METHOD OF DIAGNOSIS

[76] Inventor: David Parratt, 91 Strathern Rd., Dundee DD5 1JT, Scotland

[21] Appl. No.: 395,078

[22] PCT Filed: Oct. 23, 1981

[86] PCT No.: PCT/GB81/00232

§ 371 Date: Jun. 11, 1982

§ 102(e) Date: Jun. 11, 1982

[87] PCT Pub. No.: WO82/01593

PCT Pub. Date: May 13, 1982

[30] Foreign Application Priority Data

Oct. 24, 1980 [GB] United Kingdom ............... 8034401

[51] Int. Cl.$^4$ ........................................ G01N 33/54
[52] U.S. Cl. ........................................ 436/507; 435/7;
424/85; 424/86; 424/87; 436/509; 436/531;
436/540; 436/542; 436/804; 436/811; 436/815
[58] Field of Search ...................... 424/1.1, 85, 86, 87;
436/506, 507, 509, 501, 504, 518, 531, 538, 542,
804, 811, 540; 435/7

[56] References Cited

U.S. PATENT DOCUMENTS 4,138,213 2/1979 Masson et al. ..................... 424/1

FOREIGN PATENT DOCUMENTS 7987451 2/1981 Japan.

OTHER PUBLICATIONS

Casali et al., Clin. Exper. Immunol., vol. 29(2), pp. 342-354 (1977).
Casali et al., Protides Biol. Fluids, vol. 26, pp. 123-126 (1979a).
Casali et al., Clin. Exper. Immunol., vol. 37(2), pp. 295-309 (1979b).
Chenais et al., Protides Biol. Fluids, vol. 26, pp. 119-122 (1979).
Devey et al., J. Immunological Methods, vol. 34, pp. 191-203 (1980).
Eisenberg et al., J. Immunology, vol. 118(4), pp. 1428-1434 (1977).
Glikmann et al., Acta Pathol. Microbiol. Scand., vol. 87C (2), pp. 121-129 (1979).
Harkiss et al., Clin. Exp. Immunol., vol. 39(3), pp. 576-582 (1980).
Hautanen et al., J. Immunol. Methods, vol. 30, pp. 367-380 (1979).
Manca et al., Clin. Immunol. Immunopath., vol. 16(2), pp. 131-141 (1980).
Pereira et al., J. Immunology, vol. 125(2), pp. 763-770 (1980).
Yoshida et al., Pinsho Kensa, vol. 23(1), pp. 19-26 (1979).
Gupta et al., Clin. Expt. Immunol., vol. 46(1), pp. 9-19 (1981).
Pohl et al., J. Immunol. Methods, vol. 40, pp. 313-330 (1981).
Theofilopoulus, A. N., *Methods in Enzymology, vol. 74 (Pt. C), pp. 511-530 (1981)*.

Primary Examiner—Ben R. Padgett
Assistant Examiner—M. Moskowitz

[57] ABSTRACT

A method of diagnosis using an attached material for binding to an immune complex, by treating the bound complex with a series of different reagents or mixtures thereof and detecting the presence or absence of reaction in each case, this method being based on immune complexes produced in the body during infection and allowing much earlier detection and diagnosis of infection thereby providing the facility for treatment to reduce the damage caused to the body by the formation of complex.

10 Claims, 1 Drawing Figure

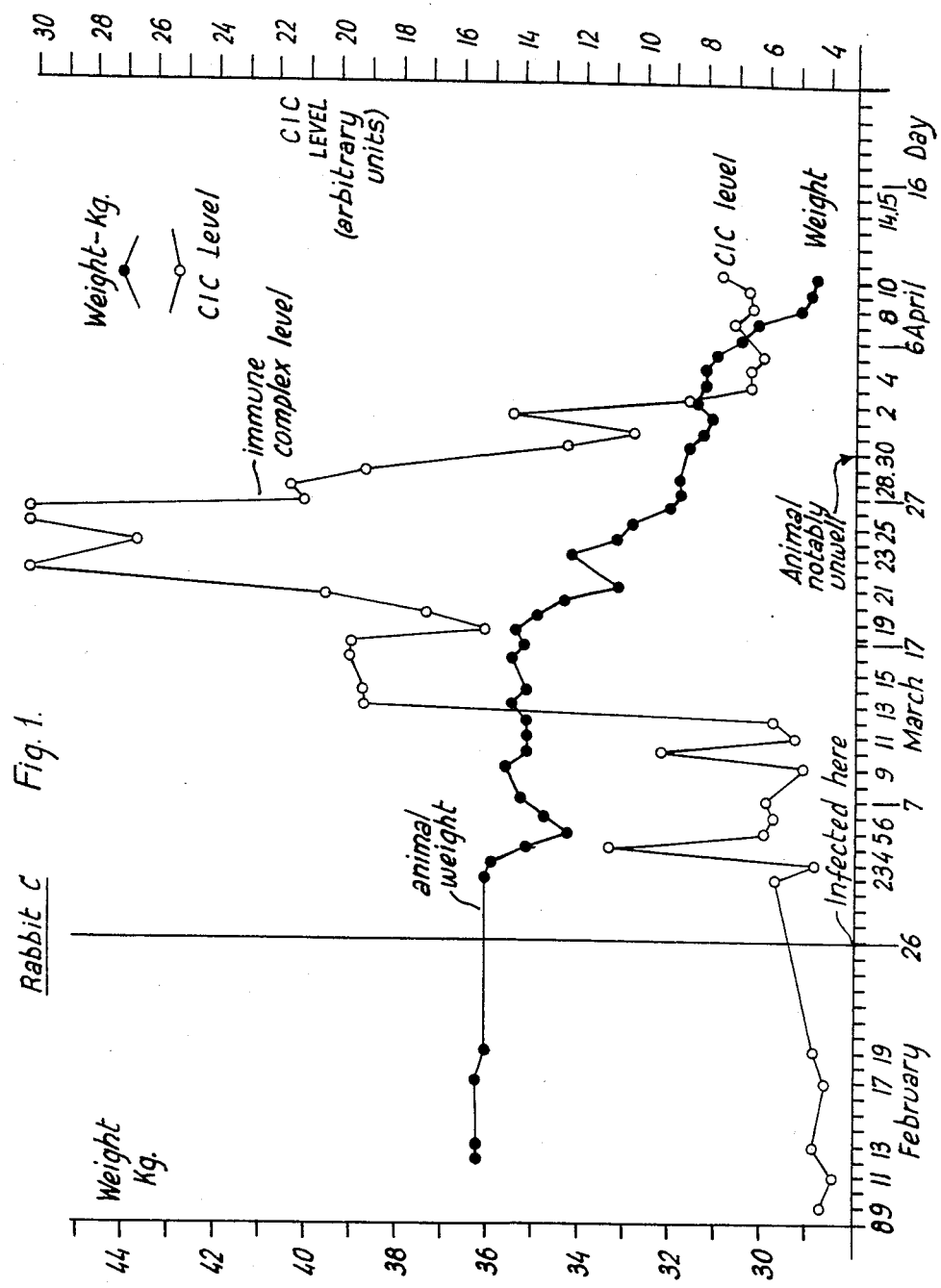

METHOD OF DIAGNOSIS

This invention relates to a method of diagnosis.

When a patient is infected by a micro-organism, or antigen, the entry of the micro-organism into the patient's bloodstream causes the production of an antibody by the patient's body and the antibody combines with an antigen from the micro-organism and with "complement", which is contained in the blood, to form an immune complex in the patient's body.

Recently immune complexes have been implicated in the aetiology of some human diseases, in particular as a cause of tissue damage, and thus the accurate measurement of complexes is of growing importance to medical practitioners. Many of the procedures currently used for their measurement rely upon interaction of complex with the complement system, for instance by virtue of the decreases in serum complement levels so caused. Alternatively, complex may be detected by measuring differences in their physico-chemical characteristics relative to uncombined antibody. These techniques, however, are generally insensitive, inaccurate, difficult to use and give little information about the antigen and antibody components of the complex. Other techniques make use of living cells or human reagents and as such are unsuitable for application on the extensive scale required by hospital laboratories.

During the initial stages of infection the patient's body contains an excess of infecting micro-organisms over antibody but as the infection proceeds the body produces more antibody until there is an excess of antibody. In the early stages only a small amount of complex is formed in view of the small amounts of antibody produced by the body, and this does not activate the complement, so little damage is caused to the body and no symptoms are detected. As the production of antibody increases however the amount of complex increases correspondingly, and as the stage approaches where the antigen and antibody are in equal proportions in the body the complex is present in substantial amounts. Moreover, it has been found that the complex produced at this stage has a half-life of about a week, so its effect is felt over a prolonged period. On passing the antigen/antibody balance point the antibody is produced in excess and it has been found that the half-life of the complex produced then is reduced to a few hours. Thereafter the antibody excess increases until the antigen and the complex are no longer present.

In general, symptoms appear in a patient only during the period of antibody excess, and this may be due to the high concentration of complex present, both of long half-life from before the antigen/antibody balance point and of short half-life from during and after the balance point. By the time that the symptoms appear, therefore, the infection is well advanced and treatment may have to be drastic. Further, the symptoms often appear after the infectious stage has been passed so that the infection may have been already passed on to others before detection.

It has previously been proposed to determine the amount of immune complex in a sample by means of an assay using conglutinin, as this material has the property of combining with an immune complex. The use of conglutinin has however been restricted to the assay.

According to the present invention there is provided a method of diagnosis comprising providing a material for attachment to an immune complex, obtaining an extract from a living body, treating the body extract with said material thereby to attach any immune complex present in the extract to said material, detecting the presence of attached immune complex, treating the attached immune complex with a series of different reagents or reagent mixtures known to react with specific immune complex components, and detecting the presence or absence of reaction between each reagent or reagent mixture and the immune complex thereby to identify the immune complex wherein the body extract is obtained from the body prior to the appearance of symptoms of infection in the body.

By using the method of this invention it is possible to test individual patients for the presence or absence of complex and to identify the complex, at an early stage of complex production in the body and before the formation of damaging long-half-life complex. This can be done in circumstances, for example, where an infection has been detected by symptoms in an individual and it is desired to prevent the infection spreading to others. Thus those individuals who have been in contact with the infected patient can be tested by the present method before symptoms appear, and isolated and treated if the diagnosis shows that they have the infection.

In an alternative example, regular diagnosis by the present method can be carried out in environments where infections could spread rapidly and with great effect, for example in schools, old peoples' homes and other places where large numbers of people come together regularly. In this example the individuals can be "screened" periodically to detect and diagnose any infections before they would otherwise become apparent and before they have reached a stage where they can be transmitted to others.

The present method also allows infections to be treated early and can reduce thereby the amount of suffering of a patient. As the infection may be detected and diagnosed before the damaging long-half-life complex is produced, antibody specific to the offending antigen can be administered in excess so that the antigen/antibody balance point is rapidly reached and passed, and only a small amount of complex having a long half-life is produced. The patient therefore would experience considerably less discomfort as the symptons would be reduced in intensity.

The material for attachment to the complex is preferably conglutinin as this is the most convenient material available at this time; however, other materials may be used if appropriate, for example immunoconglutinin or rheumatoid factor. Immunoconglutinins are naturally occurring antibodies formed against complement components in an antigen/antibody/complement complex, and conveniently react specifically with complement which has been altered by interaction with complex. Immunoconglutinins may be obtained from the sera of most animals, e.g. sheep or rabbits which have previously been challenged with suitable complexes.

The conglutinin may be prepared by treating conglutinin-containing serum with an absorbent for conglutinin, washing the treated serum to separate the absorbed conglutinin, and separating the conglutinin from the absorbent.

Preferably, the absorbent is zymosan, which may be obtained by treating baker's yeast with 0.1M 2-mercaptoethanol for 2 hours and alkylating the product with 0.02M iodacetamide in phosphate-buffered saline solution.

Preferably also the conglutinin is separated from the absorbent by centrifuging and dialysing. Purification can be by chromatography, for example by passage through Sephadex G-200.

Conglutinin advantageously reacts only with a $C_{3b}$ component of complement which has been formed after interaction with an antigen/antibody complex. Conglutinin may be obtained from the sera of ruminant animals, preferably from a euglobulin fraction of bovine serum, although it may also be obtained from the serum of other ruminants e.g. African buffalo, water buck, Uganda kob etc. In a particularly preferred method, conglutinin is extracted from bovine serum by use of zymosan, a yeast cell wall preparation. Conglutinin may also be separated from other serum constituents by gel filtration, for instance through Sephadex G-200 in the presence of mercaptoethanol and EDTA, as described by Lachman (Advances in Immunology 1976, 6, 479). Conglutinin rich preparations may be obtained by the combination of these procedures in any sequence to achieve the standard of purity desired.

The material, especially when it is conglutinin, is preferably attached to a solid substrate prior to treatment with the immune complex, and it has been found to be very effective to use as the substrate balls of plastics material such for example as those sold by Euro-Matic Limited, which offer an extensive surface area over which the material can attach itself. Alternatively the solid substrate can be in the form of a receptacle such as a dish or a test tube, or can be coated on the surface of such a receptacle.

Conglutinin and immunoconglutinin can be linked to the solid substrate by any suitable means. The conglutinin and immunoconglutinin are preferably in a purified state, though impure or partially purified forms may be used such as the complete euglobulin fraction of bovine serum. The method used to link the conglutinin or immunoconglutinin to the solid substrate may include use of a coupling reagent and/or appropriate preparation of the solid substrate. For example it has been found that conglutinin may be linked to Sephadex particles which have been activated with cyanogen bromide.

In the step of identifying the immune complex component reagents can be used which are active against either the antigen or the antibody. An effective method is to prepare mixtures of known reagents and to test samples of the immune complex against these mixtures. If a mixture is found which reacts with the component of the complex, either further mixtures or individual ingredients of that mixture can then be tested until the active ingredient is recognized, thus allowing identification of the component of the complex. Reagents active against the antigen component, known as anti-antigens, are preferably employed.

The presence or absence of reaction can for example be detected by labelling the reagent with a radioactive label, and after treatment of the immune complex testing for the presence of radioactivity. In an alternative method the reagent may be enzyme labelled, and reaction detected by adding an enzyme substrate and determining a colour change, for example by spectrophotometry.

Embodiments of the method of this invention will now be described by way of illustration in the following Examples.

EXAMPLE 1

Preparation of Conglutinin

A conglutinin-rich bovine serum is selected by a red cell clumping test, as described on pages 172 to 175 of "The Serology of Conglutination and its Relation to Disease" by Coombs et al (Blackwell, 1961). 1 liter of high titre bovine serum (1 in 640) is mixed with 150 g of zymosan for 2 hours at 4° C. The zymosan product is then washed with Veronal buffered saline solution and eluted with 0.01M PBS-EDTA for 10 minutes at room temperature. 0.5 ml/ml of yeast suspension is used. The product is then centrifuged and the supernatent liquid containing the conglutinin is dialysed against 0.5M NaCl overnight at 4° C.

The liquid then has its pH adjusted to 3.0 using N HCl and is dialysed against 0.001N HCl and 0.5M NaCl for 2 hours.

Pepsin is added to the resulting liquid in an amount of 0.5 mg per ml in 0.01N HCl to a final concentration of 2%. The solution is allowed to stand at 4° C. for 18 hours, and a buffer solution of 0.1M $Na_2HPO_4$ and 0.1N NaOH is added until a pH of 7.2 is achieved. The solution is then dialysed against 0.02M PBS-EDTA and then passed through a Sephadex G-200 chromatography column to separate out the conglutinin which is identified by the red cell test.

Assay and Diagnosis $\frac{1}{4}''$ polystyrene balls obtained from Euro-Matic Limited, are incubated in a solution of conglutinin in a carbonate buffer in an approximate concentration of 100 µg/ml, at pH 9.6. The balls, with the conglutinin on their surface, are then washed 3 times in veronal buffered saline/Tween solution (0.1% v/v), and placed in test tubes.

A standard of aggregated human IgG is prepared by aggregating IgG at 63° C. for 30 minutes, and a stock of solution at a concentration of 1000 µg/ml is diluted in 350 µl volumes to a concentration of 1 µg/ml. To each dilution is added 50 µl of fresh normal human serum, and the mixture is incubated at 37° C. for 30 minutes to allow complement fixation. The total 400 µl volumes of the standard and of the Test sample are added to the coated polystyrene balls in separate test tubes and incubated for 3 hours at room temperature. The balls in each tube are then washed 3 times with the veronal buffered saline/Tween solution at room temperature. 0.4 ml of radiolabelled anti-human immunoglobulin is added to each tube and incubated for 3 hours at room temperature, then being washed 3 times with the veronal buffered saline/Tween solution. The radioactivity of the bound immunoglobulin in the standard and test samples is then measured, the standard providing a datum for determining the presence of immune complex quantitatively in the test sample.

Having measured the level of immune complex, further identical test samples are added to conglutinin-coated balls, incubated and washed as described above. Thereafter different selected mixtures of radioactive-labelled anti-antigens, which are known antibodies against bacteria, fungi or viruses, are added to the test samples, incubated and washed as described above, and the coated balls are then tested for radioactivity using an ICN Gammaset 500 counter.

When a mixture of anti-antigens is found to have bound to the immune complex, the components of that mixture are tested individually or in further mixtures against the immune complex in the same manner until the anti-antigen which has bound to the complex is identified.

In this way not only the quantity of immune complex present in the sample but also the nature of the antigen in the complex can be determined, thus providing a quantitative and qualitative test for immune complex.

The invention as described in this Example therefore provides a diagnostic test for identifying infection in a test sample.

EXAMPLE 2

This Example shows that early detection and identification of immune complexes can be made, before symptoms are apparent. Routine samples of blood serum was obtained from two individuals, both young, apparently healthy, adult males. The samples were each subjected to assay as in Example 1, and then diagnosis was carried out by adding to the conglutinin-coated balls with the complex attached a series of non-radiolabelled anti-antigens, namely:

anti-influenza B viruses
anti-respiratory syncytial viruses
anti-adeno viruses and
anti-influenza A viruses The balls were then treated with radiolabelled sheep anti-human IgG, polyvalent reagent, and then tested for radioactivity after washing. The balls treated with anti-influenza B produced a positive result.

The antibodies used were prepared in vivo but it is equally effective to use monoclonal antibodies.

The day after sampling, both individuals developed flu-like symptoms which became worse throughout that day and into the next. By the third day they were both improving and on the fourth were able to return to work where blood samples were taken. Further blood samples were obtained 16 days later and conventional serological analysis of these (i.e. by antibody detection) confirmed that both had been infected with a strain of Influenza B virus.

The results obtained with an immune complex assay are summarised in Tables 1 and 2. The assays were carried out as described in the Example 1. Plastic balls were used to carry the conglutinin, radiolabelled sheep anti-human IgG identified the immune complexes and quantitated them, and radiolabelled rabbit anti-influenza B antibody was the anti-antigen which identified the antigen.

TABLE 1

Results of conglutinin radioimmunoassay for immune complex

| Sample | Corrected count Radioactivity in cpm | μg/ml equivalents of immune complexes |
|---|---|---|
| Standard | | |
| (1) | 23010 | 600 |
| (2) | 13590 | 300 |
| (3) | 8690 | 150 |
| (4) | 3750 | 75 |
| (5) | 3670 | 37 |
| First Patient | | |
| Day 1 | 15450* | 350* |
| Day 4 | 8710 | 190 |
| Day 20 | 480 | <75 |
| Second Patient | | |
| Day 1 | 22460* | 540* |
| Day 4 | 7900 | 170 |
| Day 20 | 600 | <75 |

TABLE 1-continued

Results of conglutinin radioimmunoassay for immune complex

| Sample | Corrected count Radioactivity in cpm | μg/ml equivalents of immune complexes |
|---|---|---|
| Normal sera | | |
| (1) | 82 | <75 |
| (2) | 306 | <75 |
| (3) | 285 | <75 |

*Denotes exceptionally high values
The assay quantitates satisfactorily between 75 and 600 μg/ml. Normals fall in the range 0–75 μg/ml

TABLE 2

Detection of influenza B antigen in immune complexes

| Sample | Radioactivity counts/min. |
|---|---|
| Normal | |
| (1) | 1360 |
| (2) | 1718 |
| First Patient | |
| Day 1 | 2221* |
| Day 4 | 1474 |
| Day 20 | 1780 |
| Second Patient | |
| Day 1 | 2444* |
| Day 4 | 1683 |
| Day 20 | 1746 |

It should be noted that the assay can be made to quantitate satisfactorily from 0–75 μg/ml, but for screening purposes, when looking for abnormal values, this is not essential.

From these results it is clear that on Day 1—i.e. one day before symptoms appeared—high levels of immune complexes were present in the blood of both individuals. The level was lower by Day 4 by which time they were recovering and by Day 20 both were normal.

The examples show that infection, even simple respiratory virus infection could be detected by the finding of abnormal levels of immune complex in the blood.

Table 2 gives the results obtained with an anti-antigen (i.e. anti-influenza B virus antibody). As can be seen, it satisfactorily identified influenza virus in the appropriate samples.

Note that antigen was only detected in the "early" phase of infection, not during recovery; this is to be expected because after recovery begins antigen clearance from the blood will be rapid.

EXAMPLE 3

Trypanosomiasis (sleeping sickness) in rabbits

New Zealand White rabbits were infected on 26th February with a clone preparation of *Trypanosoma brucei brucei* (WIG-19). Daily blood samples were taken to establish whether the animals had parasites in their blood (by Leishman-stained films and microscopy), and for immune complexes by the method described in Example 1. The weight of the animals was recorded each day and a careful watch was kept for signs of illness. A summary of the results from one representative experiment is shown in the accompanying FIG. 1.

It can be seen that after injection a progressive increase in immune complex levels occurred, reaching a peak between the 19th and 25th March. The abnormality of the animal was evident in raised immune complex levels prior to this time, and it was only later that weight reduction was seen. Symptoms appeared only about 30th March, and throughout the whole experiment trypanosomes were not observed in the blood films by microscopy. Hence the immune complexes were a very sensitive indicator of the infective process which was going on in this animal. The complex detection was with a radiolabelled sheep anti-rabbit IgG, which favours antibody excess immune complexes.

Modifications and improvements may be made without departing from the scope of the invention.

I claim:

1. A method of identifying the presence or absence of an infected state in a living body before the appearance of symptoms of the infection, comprising:
   (a) obtaining a biological fluid sample from a living body not displaying symptoms of a particular infection;
   (b) adding to the sample a material which is known to bind with immune complex characteristic of said particular infection;
   (c) adding to samples of the resulting material radiolabelled or enzyme-labelled reagents known to react specifically with antigen portions of different immune complexes, one of which is characteristic of said particular infection,
   (d) separating excess of said reagents and
   (e) detecting the presence or absence of said label in the residual mixtures thereby to identify the nature of any reacted antigen portion of immune complex characteristic of said particular infection.

2. A method according to claim 1, wherein the material which is known to bind with immune complex is selected from the group consisting of conglutinin, immunoconglutinin and rheumatoid factor.

3. A method according to claim 1, wherein the material which is known to bind with immune complex is coated on an inert solid substrate.

4. A method according to claim 3, wherein the inert solid substrate is in the form of plastic balls whose surfaces are coated with said material.

5. A method according to claim 1, wherein prior to the addition of the radiolabelled or enzyme-labelled reagents radiolabelled immunoglobulin is added to the samples of said resulting mixture for reaction with any immune complex present, excess radiolabelled immunoglobulin is separated and the presence or absence of said label is detected in the remaining reaction mixture.

6. A method according to claim 1, wherein a plurality of different radiolabelled or enzyme-labelled antibody mixtures are added one to each of the samples of said resulting mixture containing bound immune complex, excess of each of said mixtures is separated, the presence or absence of said label is detected in each sample to identify which of the mixtures has reacted with the immune complex, individual radiolabelled or enzyme-labelled antibodies of the mixture which reacted with the immune complex are then added to further samples of said resulting mixture, excess antibody is separated in each case, and the presence or absence of said label is detected in each sample to identify the antibody which has reacted with the immune complex.

7. A method according to claim 1, wherein a plurality of different antibody mixtures are added one to each of the samples of said resulting mixture containing bound immune complex, excess antibody mixture is separated in each case, a polyvalent radiolabelled or enzyme-labelled reagent known to react with the antibody is then added to each of the reaction mixtures obtained, excess polyvalent reagent is separated in each case, the presence or absence of said label in each of the reaction mixtures is then detected to identify which of the mixtures has reacted with the immune complex, individual antibodies of the mixture which reacted with the immune complex are added to further samples of said resulting mixture containing bound immune complex, excess antibody is separated in each case, polyvalent radiolabelled or enzyme-labelled reagent known to react with the antibody is then added to each of the reaction mixtures, excess polyvalent reagent is separated in each case, and the presence or absence of said label is detected in each sample to identify which of the antibodies has reacted with the immune complex.

8. A method of identifying the presence or absence of an infected state in a living body before the appearance of symptoms of the infection, comprising;
   (a) obtaining a biological fluid sample from a living body not displaying symptoms of a particular infection,
   (b) adding conglutinin to the sample to bind with immune complex characteristic of said particular infection;
   (c) adding to samples of the resulting bound conglutinin radiolabelled or enzyme-labelled reagents known to react specifically with antigen portions of different immune complexes, one of which is characteristic of said particular infection,
   (d) separating excess of said reagents and
   (e) detecting the presence or absence of said label in the residual mixtures thereby to identify the nature of any reacted antigen portion of immune complex characteristic of said particular infection.

9. A method of immunizing a living body against an infected state before appearance of symptoms of the infection, comprising:
   (a) obtaining a biological fluid sample from a living body not displaying symptoms of a particular infection;
   (b) adding to the sample a material known to bind with immune complex characteristic of said particular infection;
   (c) adding to samples of the resulting material radiolabelled or enzyme-labelled reagents known to react specifically with antigen portions of different immune complexes, one of which is characteristic of said particular infection;
   (d) separating excess of said reagents;
   (e) detecting the presence or absence of said label in the residual mixtures thereby to identify the nature of any reacted antigen portion of immune complex characteristic of said particular infection; and
   (f) introducing into said living body, before the appearance of said particular infection, antibody specific to the identified antigen portion of the immune complex.

10. A method according to claim 9, wherein the antibody is introduced in sufficient quantity to produce an excess of the antibody over the antigen in the living body.

* * * * *